United States Patent
Saeki

(10) Patent No.: US 7,227,643 B2
(45) Date of Patent: Jun. 5, 2007

(54) SURFACE PLASMON EXCITATION DEVICE AND MICROSCOPE INCLUDING THE SAME

(75) Inventor: Tetsuo Saeki, Ibaraki (JP)

(73) Assignee: Sharp Kabushiki Kaisha, Osaka (JP)

( * ) Notice: Subject to any disclaimer, the term of this patent is extended or adjusted under 35 U.S.C. 154(b) by 161 days.

(21) Appl. No.: 10/526,643

(22) PCT Filed: Sep. 8, 2003

(86) PCT No.: PCT/JP03/11460

§ 371 (c)(1),
(2), (4) Date: Mar. 3, 2005

(87) PCT Pub. No.: WO2004/029595

PCT Pub. Date: Apr. 8, 2004

(65) Prior Publication Data

US 2006/0139921 A1   Jun. 29, 2006

(30) Foreign Application Priority Data

Sep. 26, 2002 (JP) .............................. 2002-281126

(51) Int. Cl.
*G01N 21/55* (2006.01)
(52) U.S. Cl. .................. 356/445; 369/275.2; 356/446; 356/318; 385/12
(58) Field of Classification Search ........ 356/445–446, 356/311–318; 362/253; 359/569; 250/216; *F21V 33/00*
See application file for complete search history.

(56) References Cited

U.S. PATENT DOCUMENTS

| 4,997,278 A | 3/1991 | Finlan et al. |
| 5,875,032 A * | 2/1999 | Naya ..................... 356/445 |
| 2003/0048744 A1* | 3/2003 | Ovshinsky et al. ...... 369/275.2 |

FOREIGN PATENT DOCUMENTS

| JP | 1-138443 | 5/1989 |
| JP | 05-240787 | 9/1993 |
| JP | 06-167443 | 6/1994 |
| JP | 2001-311685 | 11/2001 |

OTHER PUBLICATIONS

Takayuki Okamoto, et al., "Surface plasmon microscope with electronic angular scanning", RIKEN Review No. 1, (Apr. 1993), Focused on Light Science and Technology, pp. 17-18.

* cited by examiner

*Primary Examiner*—Terrell L. McKinnon
*Assistant Examiner*—Iyabo S. Alli
(74) *Attorney, Agent, or Firm*—David G. Conlin; David A. Tucker; Edwards Angell Palmer & Dodge LLP

(57) ABSTRACT

A device for exciting surface plasmons includes a light illuminating source, a transparent substrate having a ridge, a metal layer covering side surfaces of the ridge and their neighboring region, and a thin metal film formed on a top face of the ridge. Evanescent waves caused by light emitted from the light illuminating source and transmitted through the transparent substrate and the thin metal film can excite surface plasmons in the thin metal film.

5 Claims, 4 Drawing Sheets

SURFACE PLASMON EXCITATION DEVICE AND MICROSCOPE INCLUDING THE SAME

TECHNICAL FIELD

The present invention relates to a device for exciting surface plasmons and to improvement in a microscope including the device for exciting surface plasmons.

BACKGROUND ART

In the conventional field of optics, the focal spot size has been restricted due to the diffraction limit of light. In recent years, however, near-field light that can exceed the limit has attracted attention, and investigations using the near-field light have been vigorously conducted in various fields, for example, using a scanning near field optical microscope (SNOM) capable of observing an object of nanometer size. Among the applications of the near-field light, surface plasmon resonance has particularly attracted attention, which makes it possible to obtain electric field intensity of tens of times of that of incident light. Here, the surface plasmon resonance means a phenomenon that plasma oscillation of free electrons, which are generated locally in a metal surface layer when external electromagnetic waves are applied thereto, comes to resonate with the applied electromagnetic waves.

Japanese Patent Laying-Open No. 1-138443 discloses a device for causing the surface plasmon resonance. FIG. 6 is a schematic cross sectional view of a basic device for causing the surface plasmon resonance. This device includes a light source 101, a light converging lens 102 for converging light emitted from the light source, a triangular prism 103 formed of a transparent dielectric, a thin metal film 104 formed on a surface of the triangular prism, and a photodetector 105 for detecting light reflected by the thin metal film.

P-polarized light emitted from light source 101 is transformed by light conversing lens 102 to convergent light, which is transmitted through triangular prism 103 and focused on thin metal film 104 at an incident angle θ. Incidentally, "p-polarized light" means linearly polarized light in which the electric vector of the light incident on a substance surface has a vibration direction that lies in a plane including the traveling direction of the light and a line normal to the substance surface. A part of the light focused on thin metal film 104 satisfies the resonance condition and comes to resonate with a surface plasmon to cause an enhanced evanescent field 106 on the free surface side of thin metal film 104. The remaining part of the light is reflected and then is detected by photodetector 105.

A graph shown in FIG. 7 is obtained by changing the incident angle θ of light on thin metal film 104. In this graph, a horizontal axis represents the incident angle θ of light, and a vertical axis represents reflectance (%). In FIG. 7, the intensity of light received by photodetector 105 becomes a minimum at a specific incident angle θs, indicating that a part of the convergent light resonates with a surface plasmon at that incident angle.

Japanese Patent Laying-Open No. 5-240787 discloses an application of the above-described device for exciting surface plasmons to a microscope. FIG. 8 is a schematic cross sectional view of a basic microscope utilizing surface plasmons. This figure shows a light source 201, a beam expander (lenses 202, 203) for expanding parallel light emitted from the light source, a light converging lens 204 for transforming the parallel light expanded by the beam expander into convergent light, a prism 205 for coupling the light, a thin metal film 206 formed on a surface of prism 205, a specimen 208 separated from the thin metal film with a gap filled by emulsion oil 207, a photodetector 209 for detecting the light reflected by thin metal film 206, and an X-Y pulse stage 210 for moving specimen 208 intermittently.

Parallel light emitted from light source 201 is expanded by beam expander 202, 203, and transformed by light converging lens 204 to convergent light which is then transmitted through prism 205 and focused on thin metal film 206. Of the focused light, a light part having a specific incident angle excites a surface plasmon. The incident angle depends on the thicknesses and refractive indices of thin metal film 206, emulsion oil 207 and specimen 208.

The light reflected by thin metal film 206, without contributing to excitation of the surface plasmon, is measured by photodetector 209. Photodetector 209 detects coordinates where intensity of the reflected light is reduced due to excitation of the surface plasmon, and then a surface plasmon excitation angle can be obtained from the coordinates, thereby making it possible to determine change in refractive index of specimen 208. Further, X-Y pulse stage 210 is used to scan specimen 208 so as to obtain two-dimensional distribution of the refractive index of the specimen.

With the device shown in FIG. 6 or FIG. 8, however, the area where the surface plasmon is excited depends on the spot size of the focused light. For example, in FIG. 6, if light source 101 has a wavelength of 650 nm and light converging lens 102 has an NA (numerical aperture) of 0.6, the light beam can be narrowed only to a diameter of about 1 μm. This means that the microscope of FIG. 8 can obtain a resolution only on the order of 1 μm. That is, the resolution limit of a microscope is determined by the diffraction limit of light emitted from the light source.

On the other hand, it is possible to reduce the spot size to a certain degree by decreasing the wavelength of the source light and increasing the NA of the light converging lens. However, it is extremely difficult to obtain a small light spot of an nm order size. Thus, it appears that the resolution of the conventional microscope utilizing surface plasmons has already reached a critical limit.

DISCLOSURE OF THE INVENTION

In view of the above-described situations of the conventional art, an object of the present invention is to provide a device that can excite surface plasmons in a micro area and to provide a high-resolution microscope utilizing the device.

A device for exciting surface plasmons according to the present invention includes a light illuminating source, a transparent substrate having a ridge, a metal layer covering side surfaces of the ridge and the neighboring regions, and a thin metal film formed on a top face of the ridge, wherein evanescent waves caused by light emitted from the light illuminating source and transmitted through the transparent substrate and the thin metal film can excite surface plasmons in the thin metal film.

Preferably, the ridge of the substrate is formed in a striped manner, and the light emitted from the light illuminating source is linearly polarized in a plane that includes a longitudinal direction and a normal direction of the top face of the ridge stripe. Still preferably, the light emitted from the light illuminating source is convergent light.

Preferably, the shape and dimensions and refractive index of the ridge, and the metal layer are set such that light emitted from the light illuminating source and directed to the ridge reaches the thin metal film in an area smaller than a width of the ridge.

Preferably, the metal layer is formed of a conductor, and the thin metal film is formed of one of gold, silver, copper and aluminum.

A surface plasmon microscope according to the present invention includes the device for exciting surface plasmons described above, a photodetector for receiving light reflected by the thin metal film and the metal layer included in the device, and a movable support for positioning a surface of a specimen in the vicinity of the thin metal film and for scanning the surface of the specimen.

BEST MODES FOR CARRYING OUT THE INVENTION

Figure 1:
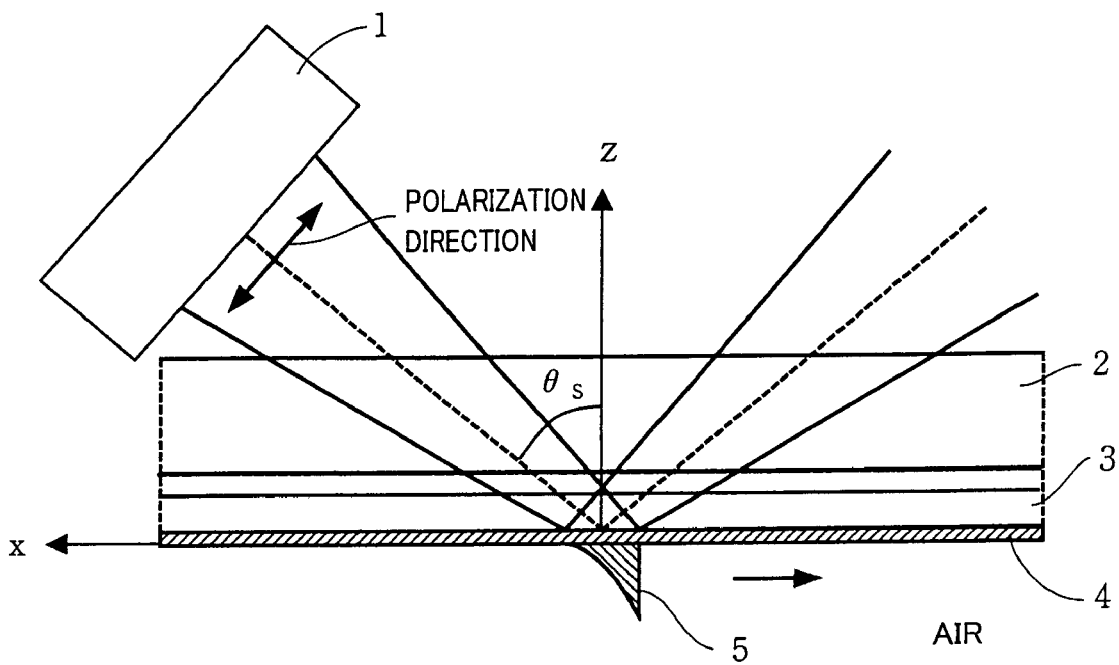
FIG. 1 is a schematic cross sectional view of a device for exciting surface plasmons according to an embodiment of the present invention.
Figure 2:
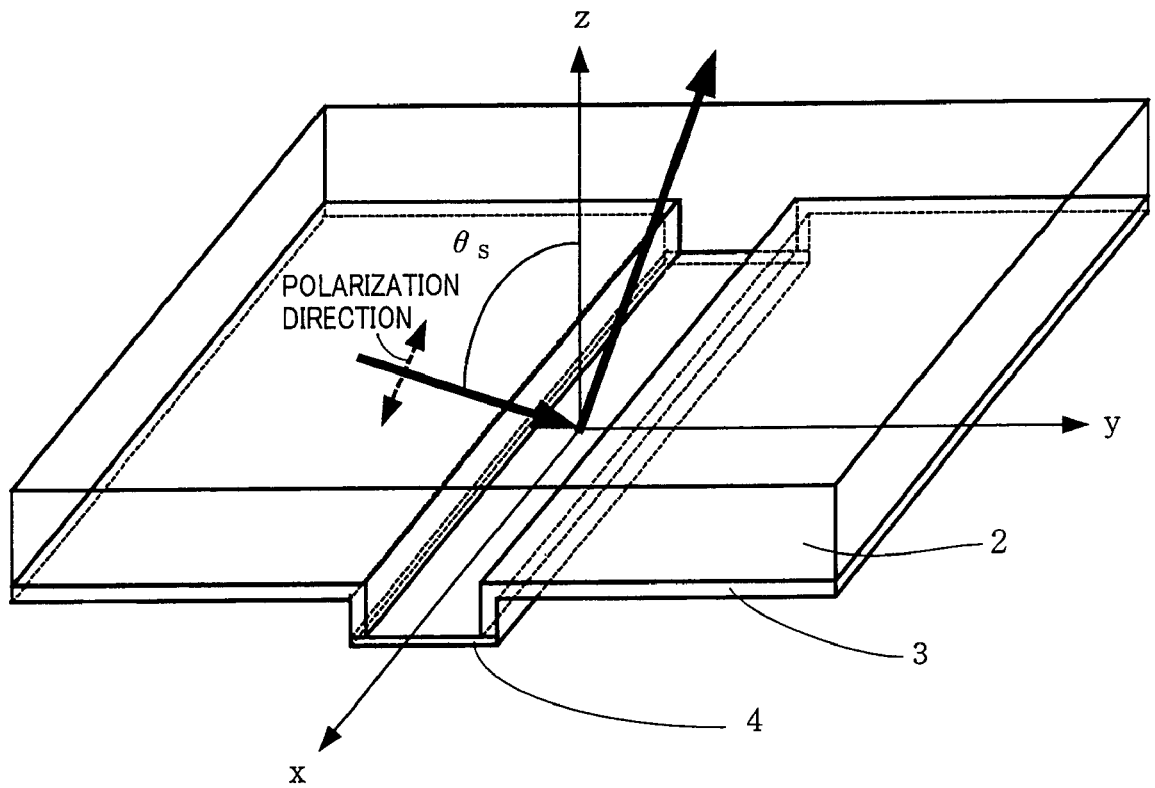
FIG. 2 is a schematic perspective view of the device for exciting surface plasmons according to the embodiment of the present invention.

A device for exciting surface plasmons according to an embodiment of the present invention is schematically shown in a cross sectional view in FIG. 1 and in a perspective view in FIG. 2. FIG. 1 corresponds to a cross section at the x-z plane in FIG. 2. Throughout the figures, the same reference characters denote the same or corresponding portions.

This device for exciting surface plasmons includes a light illuminating source 1, a transparent substrate 2 having a striped ridge, a metal layer 3 formed to cover side surfaces and the neighboring regions of the ridge, and a thin metal film 4 formed on a top face of the ridge. Here, metal layer 3 and thin metal film 4 are preferably formed of gold that hardly deteriorates with age and can reduce the propagation distance of surface plasmons. Further, for the purpose of exciting surface plasmons, thin metal film 4 is formed to have a thickness such that the incident light can be transmitted through thin metal film 4 so as to cause an evanescent field.

The convergent light emitted from light illuminating source 1 and linearly polarized in the x-z plane is transmitted through substrate 2 and enters the inside of the ridge. At this time, the light emitted from light illuminating source 1 is set to have an incident angle θs with which the surface plasmon is excited in thin metal film 4 formed on the top face of the ridge. Further, the cross sectional shape and dimensions of the striped ridge, and the materials of metal layer 3 and thin metal film 4 are set such that the incident light reaches a micro area on thin metal film 4. The light having reached the micro area of thin metal film 4 formed on top of the ridge and linearly polarized in the x-z plane causes evanescent waves 5 enhanced by the surface plasmon resonance. These evanescent waves propagate in the −x direction along the surface of thin metal film 4 on the side exposed to the air.

Figure 3:
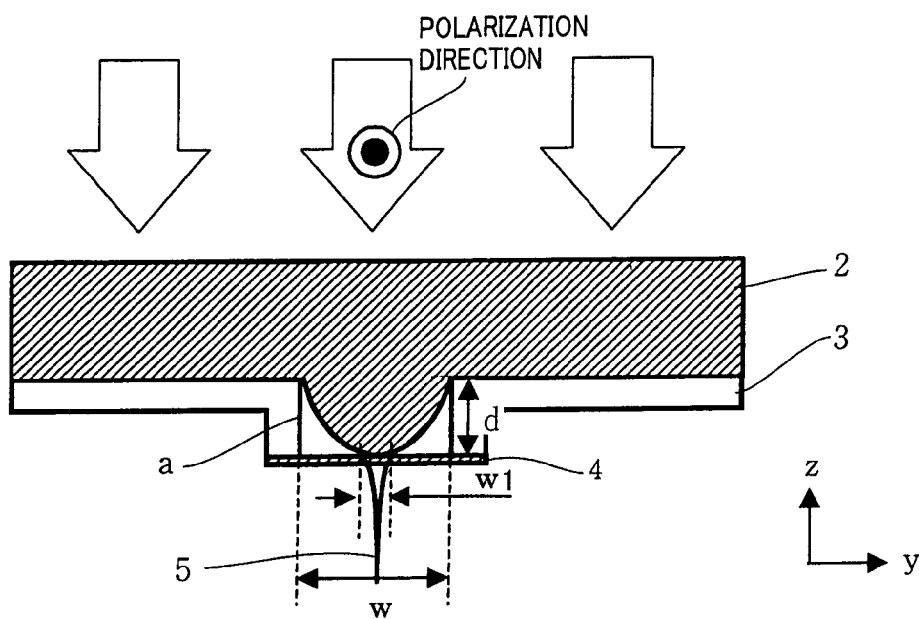
FIG. 3 is a schematic cross sectional view illustrating an area where light can exist in the device for exciting surface plasmons according to the embodiment of the present invention.

Here, specific explanation is given as to how the shape and dimensions of the ridge are determined. In FIG. 3, shaded part in the ridge represents an area where light can exist in the case that light linearly polarized in the x-z plane is incident on substrate 2. As seen from this figure, when the light linearly polarized in the x-z plane enters the inside of the ridge having its side surfaces covered with metal layers 3, the electric field parallel to the side surface "a" of the metal layer cannot exist in the vicinity of the side surface "a". Further, in the vicinity of side surface "a" of the metal layer, the area where the light can exist decreases as the light advances in the −z direction. Still further, if the depth "d" inside the ridge is greater than a certain value, the light can enter only partway inside the ridge.

Figure 4:
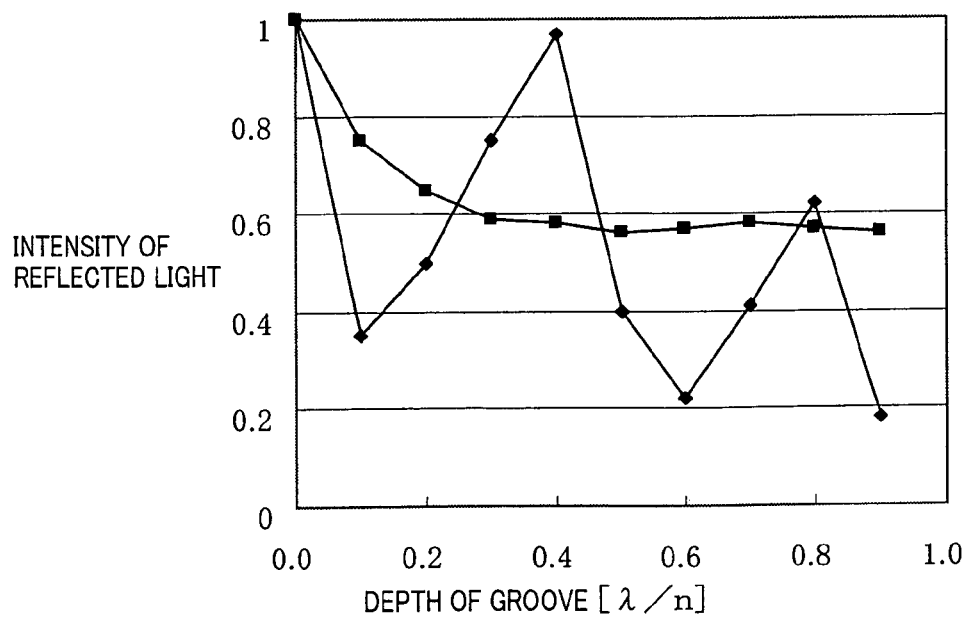
FIG. 4 is a graph showing the relation between the metal groove depth and the reflected light intensity in the device for exciting surface plasmons according to the embodiment of the present invention.

Such a phenomenon can be confirmed from the following analysis. The graph in FIG. 4 shows the relation between the depth of the metal groove and the intensity of reflected light with respect to the incident polarized light in the case that the substrate has a refractive index n of 1.58, the metal groove has a width of 250 nm, the medium forming the metal groove is gold, the incident light has a wavelength λ of 650 nm, the objective lens has an NA of 0.6, and the incident angle of light to the bottom of the metal groove is 0° (i.e., perpendicular to the substrate surface). In this graph, a horizontal axis represents the depth of the groove normalized with λ/n, and a vertical axis represents the intensity of the reflected light normalized with the intensity of the incident light. Although the medium forming the metal groove is gold in FIG. 4, the graph will show similar tendencies even if another metal such as silver, copper, aluminum or the like is employed.

Referring to FIG. 4, in the case of the light (shown with the symbol ♦ in the graph) polarized in the direction perpendicular to the side surfaces of the groove, the electric field of the incident light can exist in the vicinity of the side surfaces of the metal groove. Thus, there occurs a relative phase difference between the reflected light from the top level part of the groove and the reflected light from the bottom level part of the groove depending on the depth of the groove, and as a result, the intensity of the reflected light changes due to interference of the lights. By comparison, in the case of the light (shown with the symbol ■ in the graph) polarized in the direction parallel to the side surface of the metal groove, it is seen that the intensity of the reflected light becomes almost constant with the groove depth exceeding 0.3 λ/n. This means that, when the metal groove is deep, the light polarized parallel to the side surface of the metal groove enters only to the depth of about 0.3 λ/n.

Thus, it is possible to form a ridge allowing the incident light to reach only a micro area w1 of thin metal film 4 by setting, e.g., the wavelength λ of light illuminating source 1 to 650 nm and the height d and the width w of the ridge to 0.3 λ/n and 250 nm, respectively. Although the incident angle is 0° in this example, it is possible to form, even with the incident angle of θs, a ridge that allows the incident light to reach only a micro area w1 of thin metal film 4.

Accordingly, when the incident light is polarized in the x-z plane, surface plasmons can be excited in thin metal film 4, at a desired height d of the ridge and in an area smaller than the width of the ridge. However, if the light polarized perpendicular to the x-z plane enters, it will reach over the entire width of thin metal film 4 on the top face of the ridge, in which case it is not possible to excite the surface plasmons in thin metal film 4 in an area smaller than the width of the ridge.

As understood from the above description, according to the present invention, it is possible to excite surface plasmons within a width smaller than that of the ridge, irrespective of the width of the incident light. When this is applied to a surface plasmon microscope for example, it is possible to improve the resolution of the microscope.

Figure 5:
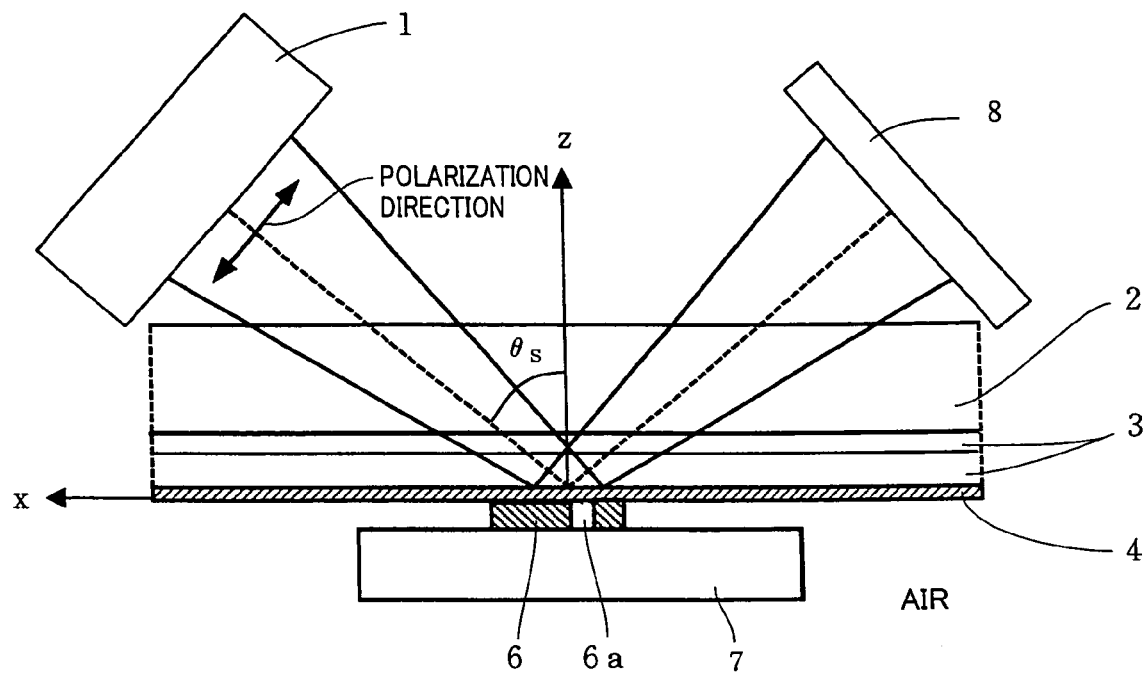
FIG. 5 is a schematic cross sectional view of a surface plasmon microscope according to another embodiment of the present invention.
Figure 6:
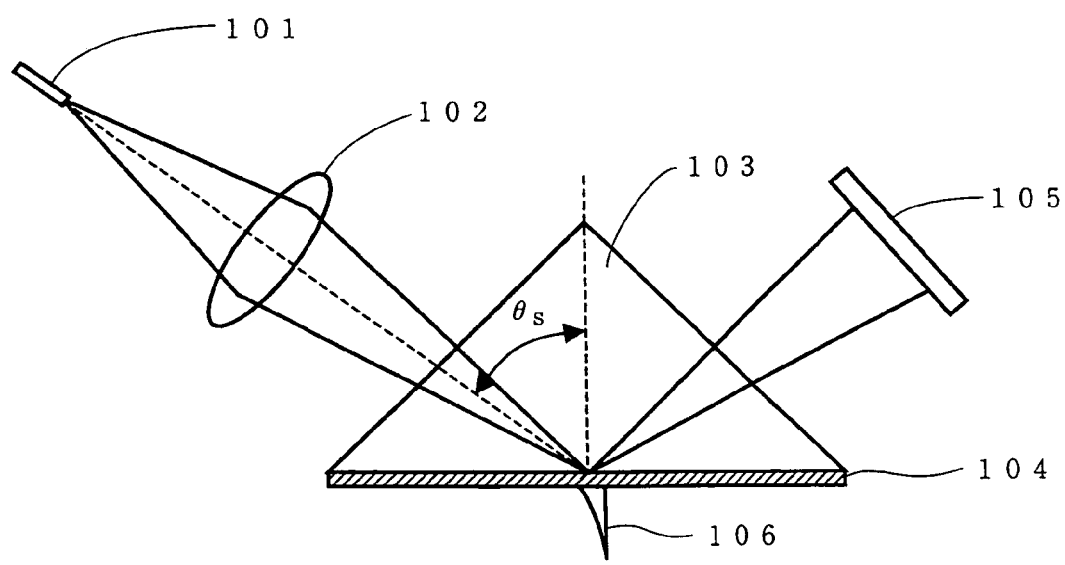
FIG. 6 is a cross sectional view of a conventional device for exciting surface plasmons.
Figure 7:
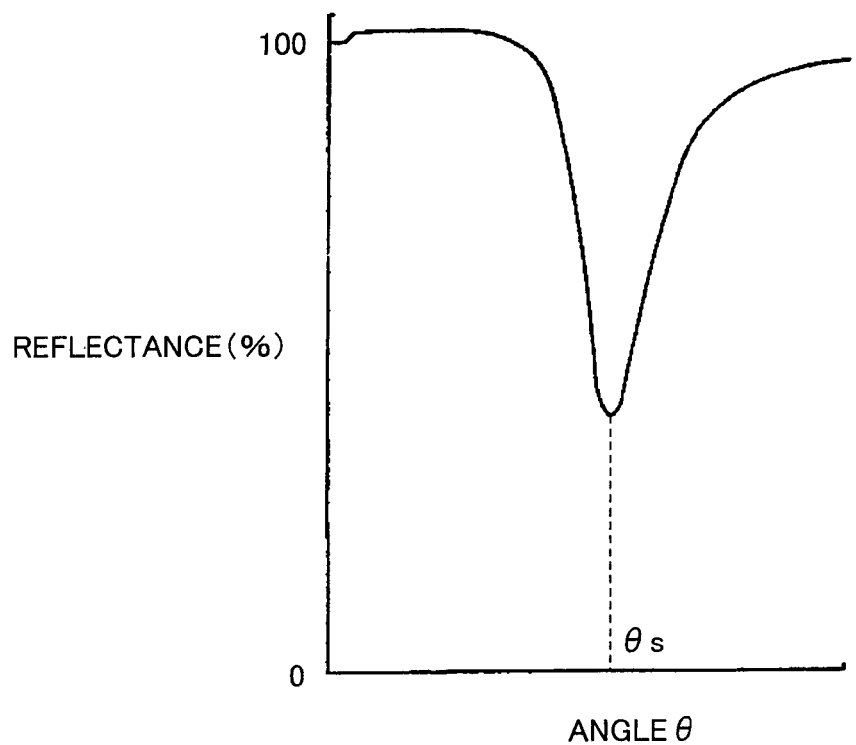
FIG. 7 is a graph showing the relation between the incident angle and the reflectance of light in the conventional device for exciting surface plasmons.
Figure 8:
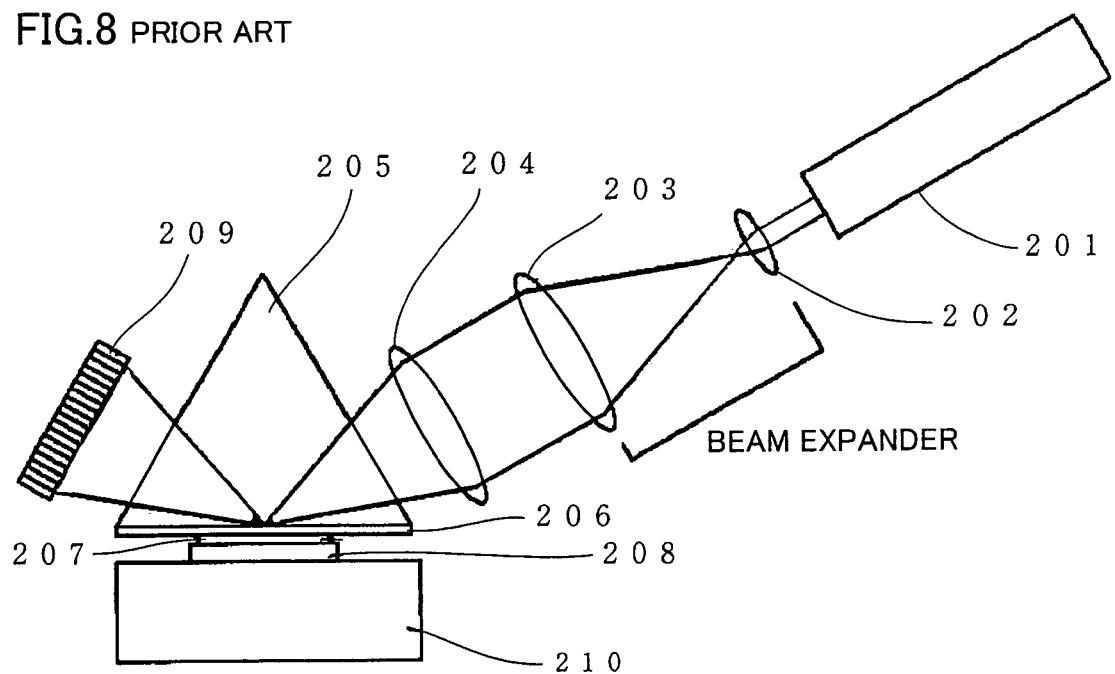
FIG. 8 is a cross sectional view of a conventional surface plasmon microscope.

The schematic cross sectional view shown in FIG. 5 illustrates a surface plasmon microscope according to another embodiment of the present invention. This figure shows a light illuminating source 1, a substrate 2 having a striped ridge, a metal layer 3 formed to cover side surfaces of the ridge, a thin metal film 4 formed on a top face of the ridge, a photodetector 8 for detecting light reflected by metal layer 3 and thin metal film 4, a specimen 6 spaced from thin metal film 4 with a gap filled with matching oil (not shown), and a movable stage 7 for scanning the specimen.

The convergent light emitted from light illuminating source 1 is transmitted through substrate 2 and focused on thin metal film 4. Of the focused light, a light part having a specific incident angle, which depends on the thicknesses and refractive indices of thin metal film 4, emulsion oil and specimen 6, excites a surface plasmon. Photodetector 8 detects light reflected by metal layer 3 and thin metal film 4 and not contributing to excitation of the surface plasmon. The coordinates at which the intensity of reflected light is reduced due to the surface plasmon excitation is detected on photodetector 8 and the surface plasmon excitation angle is calculated from the coordinates, to thereby obtain the refractive index of specimen 6.

Further, movable stage 7 is employed to scan specimen 6 so as to obtain the two-dimensional distribution of the refractive index. For example, if there is a micro area 6a in specimen 6 having a locally different refractive index, then the position of that area can be detected. At this time, a surface plasmon is excited by the device for exciting surface plasmons only in a restricted area having a width smaller than that of the ridge by virtue of the structure of the ridge, and accordingly, it is possible to improve the resolution compared to a conventional microscope.

Although the device for exciting surface plasmons having the striped ridge has been described in the above embodiments, a ridge having its length limited in the x direction, such as an information pit of an optical disk, may be utilized as well. In this case, the propagation distance of the surface plasmon (or of the enhanced evanescent waves) can be restricted, and thus, the area where the surface plasmon is excited can further be reduced in size in the x direction.

Further, in the above-described embodiments, the height d of the ridge having the rectangular cross section is changed to control the size of the area where the light reaches the thin metal film formed on the top face of the ridge. Alternatively, the width w of the ridge, metal medium, cross sectional shape of the ridge and the like may be changed to control the same.

Furthermore, according to the present invention, it is possible to reduce the size of the area where the surface plasmon is generated. Thus, its application to a sensor measuring a change in refractive index, for example, enables sensing of a micro area. Still further, the ridges may be arranged in an array and the specimens also in a corresponding array, to enable measurements of changes of refractive indices in micro areas of a great number of specimens. The present invention may further be applied to a device for measuring fluorescent reaction such as a biochip, to detect fluorescence of objects arranged in high density in a micro area, as in the case of a sensor.

INDUSTRIAL APPLICABILITY

As described above, according to the present invention, it is possible to provide a device that can excite surface plasmons in a micro area and to provide a high-resolution microscope utilizing that device.

The invention claimed is:

1. A device for exciting surface plasmons, including light illuminating means, a transparent substrate having a ridge formed in a striped manner, a metal layer covering side surfaces of said ridge and their neighboring region, and a thin metal film formed on a top surface of said ridge,
    wherein said light illuminating means is arranged so as to illuminate said ridge with light which is linearly polarized in a plane that includes a longitudinal direction and a normal direction of the top surface of said striped ridge, said metal layer is provided for gradually narrowing a width of said light advancing in a depth direction in said ridge, and
    evanescent waves caused by said light are transmitted through said transparent substrate and said thin metal film can excite surface plasmons in said thin metal film.

2. The device for exciting surface plasmons according to claim 1, wherein the light emitted from said light illuminating means is convergent light.

3. The device for exciting surface plasmons according to claim 1, wherein shape and dimensions and refractive index of said ridge, and said metal layer are set such that the light emitted from said light illuminating means and directed to said ridge reaches said thin metal film in an area smaller than a width of said ridge.

4. The device for exciting surface plasmons according to claim 1, wherein said metal layer is formed of a conductor, and said thin metal film is formed of one of gold, silver, copper and aluminum.

5. A surface plasmon microscope, including the device for exciting surface plasmons as recited in claim 1, a photodetector for receiving light reflected by said thin metal film and said metal layer, and movable support means for positioning a surface of a specimen in the vicinity of said thin metal film and for scanning the surface of the specimen.

* * * * *